United States Patent [19]
Pope, Jr.

[11] 4,406,346
[45] Sep. 27, 1983

[54] STETHOSCOPE WITH ONE-HANDED HEADSET OPERATION

[75] Inventor: Janson M. Pope, Jr., Palmdale, Calif.

[73] Assignee: Marvin A. Clark, Palmdale, Calif. ; a part interest

[21] Appl. No.: 367,383

[22] Filed: Apr. 12, 1982

[51] Int. Cl.³ ............................................... A61B 7/02
[52] U.S. Cl. ................................................... 181/131
[58] Field of Search .................... 181/20, 128–130, 181/131; 179/1 ST

[56] References Cited

U.S. PATENT DOCUMENTS

| | | | |
|---|---|---|---|
| 257,487 | 5/1882 | Food | 181/131 |
| 4,149,610 | 4/1979 | Saiya et al. | 181/131 |

Primary Examiner—Benjamin R. Fuller
Attorney, Agent, or Firm—Poms, Smith, Lande & Rose

[57] ABSTRACT

A stethoscope normally includes two tubular members which are pivotally mounted together and which have ear pieces on one end; and the headset is normally mounted on the head of the doctor or other user by using two hands, one on each of the two pivoted tubular members, and placing the ear pieces in the ears. A spring is normally connected to the other end of the head set and this spring will normally bias the tubular members and ear pieces toward one-another so that the head set will stay on the user's ears by itself. In accordance with the present disclosure, the two tubular members of the headset are provided with extensions which extend in the direction away from the ear pieces beyond the spring or the pivot point so that the ear pieces may be opened and the headset held with one hand as it is being put on or taken off from the ears of the user.

8 Claims, 1 Drawing Figure

STETHOSCOPE WITH ONE-HANDED HEADSET OPERATION

FIELD OF THE INVENTION

This invention relates to medical stethoscopes.

BACKGROUND OF THE INVENTION

Stethoscopes normally include a diaphragm-type pickup element which translates pressure changes which appear at the diaphragm into sound waves which travel through a relatively small diameter flexible sound path through a Y-junction and then through two semi-rigid tubular members to ear pieces intended for supplying the sounds to the ears of the doctor or other user. The two semi-rigid members to which the ear pieces are connected are normally pivotally mounted, often by a thin leaf spring which biases the two ear pieces toward one another so that they do not drop off the ears of the user.

One problem in the use of conventional stethoscopes is that they must normally be mounted on the head of the user using two hands, one holding on to each of the two tubular members; and they must be removed the same way. This is often inconvenient, when the doctor or other user wishes to perform other functions with one of his hands.

Accordingly, a principal object of the present invention is to provide a stethoscope which may be readily mounted on the ears of the user using only one hand; and may be removed from the ears of the user in the same one-handed manner.

SUMMARY OF THE INVENTION

In accordance with the present invention a conventional type of stethoscope may be provided with extensions which extend away from the ear pieces beyond the pivot point of the two tubular members carrying the ear pieces and which are separated by a suitable distance so that when pressure is applied to these two extensions, the ear pieces may be separated and the stethoscope head set mounted on or removed from the user's ears. The extensions may be either integral with the semi-rigid or rigid tubular members to which the ear pieces are secured, or may be separate additional elements.

Other objects, features, and advantages of the invention will become apparent from a consideration of the following detailed description and from the accompanying drawing.

BRIEF DESCRIPTION OF THE DRAWINGS

The single FIGURE of the drawings shows a stethoscope illustrating the principles of the invention.

DETAILED DESCRIPTION

Figure 1:
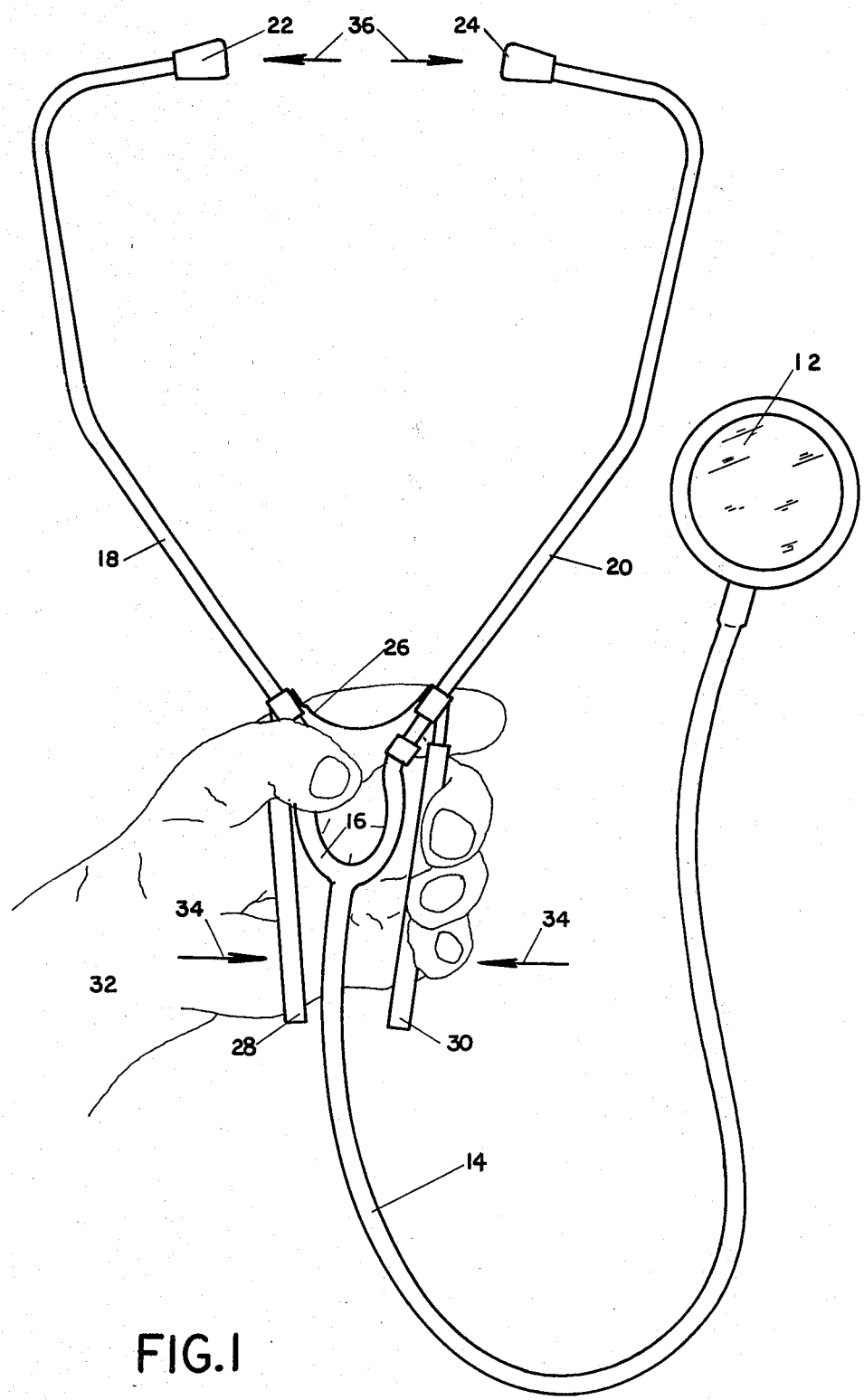

Referring to the single FIGURE of the drawings, the diaphragm type pickup element 12 is connected by a flexible rubber tube 14 to a Y-junction 16, and each of the two tubes from the Y-junction are connected to one of the two chromium plated tubes 18 and 20. Secured to the upper ends of the tubes 18 and 20 are the plastic ear pieces 22 and 24, respectively.

The two tubular members 18 and 20 are pivotally mounted to one another by the thin flat leaf spring 26. This leaf spring 26 is fairly broad, for example, one-quarter inch or so, and normally biases the ear pieces 22 and 24 so that they are spaced apart by only one-half inch or an inch, substantially less than the normal six to eight inches between the ears of a user, where the ear pieces 22 and 24 are located while the stethoscope is in use.

Using a conventional stethoscope, the doctor or other user will normally grip one of the two members 18 or 20 in each hand and, using both hands, will mount the headset in his ears. Removal would normally be accomplished in the same manner using two hands.

In one illustrative embodiment, the present invention involves the addition of the rigid member 28 and 30 which are firmly secured to and mechanically integral with the headset members 18 and 20. These members 28 and 30 extend well below the pivot for the members 18 and 20 which is located centrally on the spring 26. Accordingly, when the hand 32 of a user applies inwardly directed force as indicated by arrows 34 to the members 28 and 30, the ear pieces are separated as indicated by the arrows 36 against the normal biasing force of spring 26, and the ear pieces 22 and 24 may be readily mounted onto the user's ears. Similarly, when it is desired to take the headset off, the members 28 and 30 may be engaged once more by the hand 32, the ear pieces 22 and 24 may be separated, and the headset removed, using only one hand.

For ease in holding the members 28 and 30, they may be formed of tubular metal rods and may have rubber or plastic exterior gripping handles.

It is to be understood that the foregoing description and the accompanying drawings relate to one illustrative embodiment of the invention. Other arrangements are within the scope of the present invention. Thus, by way of example, but not of limitation, the tubular members 18 and 20 may extend downwardly and turn outwardly so that these tubular members which contain the inner sound channel or duct, may serve the function of the separate members 28 and 30 in the showing of FIG. 1. With this arrangement, the Y-shaped junction would be located at a lower point in the assembly, and the two upwardly extending tubes which lead from the Y-junction would be somewhat longer to accommodate the varying positions of the lower ends of the tubes, as they are actuated to change the spacing of the ear pieces 22 and 24. In addition, instead of employing chromium plated metal tubes 18 and 20, these members may be made of high quality plastic having sufficient rigidity to hold themselves in place in a person's ears, and the function of the spring 26 may be accomplished by the deformation of a suitable plastic element, or by using a separate pivot point and spring arrangement. Accordingly, the present invention is not limited to that precisely as shown and described hereinabove.

What is claimed is:

1. A stethoscope assembly wherein the headset may be mounted on the ears using only one hand, comprising:
    means including a pickup element for sensing pressure changes such as the heart beat at an artery or the like;
    first and second ear pieces for application to the ears of a user;
    first and second tubular members of substantial stiffness pivotally mounted to one another, and each said tubular members having one of said ear pieces affixed to one end thereof;
    means for mechanically biasing said ear pieces toward one another;

flexible tubular means for coupling said pickup element to the other end of each of said tubular members; and said stethoscope assembly including means having significant rigidity, mechanically integral with each of said tubular members, and extending in the direction away from said ear pieces beyond said pivot point, for separating said ear pieces against the force of said biasing means with only one hand, to mount the stethoscope on the ears of the user or to remove the stethoscope from the ears of the user with only one hand.

2. A stethoscope assembly as defined in claim 1 wherein said separating means includes a pair of actuating handles normally spaced apart by two to three and one-half inches when said ear pieces are biased close together.

3. A stethoscope assembly as defined in claim 1 wherein said separating means includes a pair of actuating handles normally spaced apart by about three inches when said ear pieces are biased close together.

4. A stethoscope assembly as defined in claim 1 wherein said separating means includes first and second handles and means for mounting said handles so that the ends thereof closely approach one-another when said ear pieces are spaced apart by a distance in the order of six to eight inches for locating the ear pieces in the ears, or for removing them.

5. A stethoscope assembly as defined in claim 1 wherein said separating means includes first and second handles rigidly secured to said first and second tubular members adjacent the ends of said tubular members opposite the ends of said tubular members to which said ear pieces are connected.

6. A stethoscope assembly as defined in claim 1 wherein said separating means includes first and second actuating members which are substantially parallel and spaced apart by about two to three and one-half inches when said ear pieces are close together, and means for mounting said actuating members so that their outer ends approach close to one-another when the ear pieces are separated by six to eight inches for mounting or removing from the head of a user.

7. A stethoscope assembly wherein the headset may be mounted on the ears using only one hand, comprising:

means including a pickup element for sensing pressure changes such as the heartbeat at an artery or the like;

first and second ear pieces for application to the ears of a user;

first and second tubular members of substantial stiffness pivotally mounted to one another, and each said tubular members having one of said ear pieces affixed to one end thereof;

means for mechanically biasing said ear pieces toward one-another;

flexible tubular means for coupling said pickup element to the other end of each of said tubular members; and said stethoscope assembly including means having significant rigidity attached to each of said tubular members, and extending in the direction away from said ear pieces beyond said pivot point, for separating said ear pieces against the force of said biasing means with only one hand, to mount the stethoscope on the ears of the user or to remove the stethoscope from the ears of the user with only one hand.

8. A stethoscope assembly as defined in claim 7 wherein said separating means includes first and second actuating members which are substantially parallel and spaced apart by about two to three and one-half inches when said ear pieces are close together, and means for mounting said actuating members so that their outer end approach close to one-another when the ear pieces are separated by six to eight inches for mounting or removing from the head of a user.

* * * * *